(12) United States Patent
Husmark et al.

(10) Patent No.: US 11,168,444 B2
(45) Date of Patent: Nov. 9, 2021

(54) FIBROUS PRODUCT (71) Applicant: Essity Hygiene and Health Aktiebolag, Gothenburg (SE)

(72) Inventors: Ulrika Husmark, Gothenburg (SE); Lars-Erik Enarsson, Sundsvall (SE); Caroline Severinson, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 17/055,159

(22) PCT Filed: May 15, 2018

(86) PCT No.: PCT/SE2018/050500
§ 371 (c)(1),
(2) Date: Nov. 13, 2020

(87) PCT Pub. No.: WO2019/221647
PCT Pub. Date: Nov. 21, 2019

(65) Prior Publication Data
US 2021/0189654 A1 Jun. 24, 2021

(51) Int. Cl.
*D21H 11/16* (2006.01)
*D21H 23/28* (2006.01)
*D21H 27/00* (2006.01)
*D21H 27/30* (2006.01)
*D21H 11/02* (2006.01)
*D21H 11/08* (2006.01)
*D21H 23/50* (2006.01)
*D21H 23/56* (2006.01)
*D21H 25/06* (2006.01)

(52) U.S. Cl.
CPC ............ *D21H 11/16* (2013.01); *D21H 11/02* (2013.01); *D21H 11/08* (2013.01); *D21H 23/28* (2013.01); *D21H 23/50* (2013.01); *D21H 23/56* (2013.01); *D21H 25/06* (2013.01); *D21H 27/005* (2013.01); *D21H 27/30* (2013.01)

(58) Field of Classification Search
CPC ...... D21H 27/002; D21H 27/30; D21H 27/40; D21H 27/005; D21H 11/16; D21H 11/02; D21H 11/08; D21H 23/28; D21H 23/50; D21H 23/56; D21H 25/06; A61F 13/8405; A61F 2013/8411; A61F 2013/8455; A47K 10/16; A61K 31/19; A61K 8/36; D04H 1/593
See application file for complete search history.

(56) References Cited

U.S. PATENT DOCUMENTS

| | | | |
|---|---|---|---|
| 5,807,364 A | 9/1998 | Hansen | |
| 9,962,324 B2 * | 5/2018 | Husmark | A61Q 17/00 |
| 11,000,162 B2 * | 5/2021 | Saas | D21H 27/32 |
| 2003/0143262 A1 * | 7/2003 | Brusk | A61K 8/0208 424/443 |
| 2004/0241151 A1 * | 12/2004 | Husmark | A61L 15/36 424/93.45 |
| 2005/0010183 A1 | 1/2005 | Miller et al. | |
| 2008/0115898 A1 * | 5/2008 | Gelli | B32B 29/005 162/109 |
| 2011/0224637 A1 | 9/2011 | Edgett et al. | |
| 2012/0111519 A1 * | 5/2012 | Toubeau | D21H 27/007 162/149 |
| 2012/0160436 A1 * | 6/2012 | Zwick | C11D 3/046 162/158 |
| 2012/0297560 A1 * | 11/2012 | Zwick | C11D 17/042 15/104.93 |
| 2014/0073613 A1 * | 3/2014 | Sundbom Nilsson | A61K 31/047 514/162 |
| 2015/0330029 A1 * | 11/2015 | Ramaratnam | B32B 3/30 15/104.93 |
| 2016/0128921 A1 * | 5/2016 | Husmark | A61L 15/50 424/93.4 |
| 2016/0303002 A1 * | 10/2016 | Cunningham | A61K 8/0208 |
| 2018/0064587 A1 | 3/2018 | Stahl | |
| 2018/0140529 A1 * | 5/2018 | Miller, IV | A61K 8/66 |
| 2019/0021553 A1 * | 1/2019 | Saas | D21H 27/002 |
| 2020/0170854 A1 * | 6/2020 | Husmark | A61L 15/22 |
| 2021/0189654 A1 * | 6/2021 | Husmark | D21H 27/30 |

FOREIGN PATENT DOCUMENTS

| | | | |
|---|---|---|---|
| CN | 107405234 A | 11/2017 | |
| RU | 2477149 C1 | 3/2013 | |
| RU | 2499600 C1 | 11/2013 | |
| RU | 2553294 C2 | 6/2015 | |
| RU | 2567693 C2 | 11/2015 | |
| RU | 2625433 C1 | 7/2017 | |
| WO | 9908555 A1 | 2/1999 | |
| WO | 2008058563 A1 | 5/2008 | |
| WO | 2016148612 A1 | 9/2016 | |
| WO | 2017129240 A1 | 8/2017 | |
| WO | WO-2017129240 A1 * | 8/2017 | ............ D21H 27/32 |
| WO | WO-2019221647 A1 * | 11/2019 | ............ A61L 15/20 |

OTHER PUBLICATIONS

Essity Hygiene and Health AB, Response to International Search Report and the Written Opinion, dated Jan. 23, 2019 (97 pages).
(Continued)

*Primary Examiner* — Jose A Fortuna
(74) *Attorney, Agent, or Firm* — Wood Herron & Evans LLP (57) ABSTRACT

Fibrous products having an improved softness are provided, which have beneficial effects on the skin upon use. The fibrous product includes a fibrous material in which this material has at least one of lactic acid or a salt thereof in an amount of, per ply provided, in the range of from about 0.1 to about 15 g/m$^2$, and in some embodiments, in the range of from about 1.0 to about 1.5 g/m$^2$. A water activity of the fibrous product is from about 0.03 to 0.85. The salt of lactic acid may, for example, be sodium lactate, potassium lactate, and/or calcium lactate.

18 Claims, 4 Drawing Sheets

(56) References Cited

OTHER PUBLICATIONS

Essity Hygiene and Health AB, Response to Written Opinion, dated Jan. 9, 2020 (8 pages).
Essity Hygiene and Health AB, Response to the second Written Opinion, dated Mar. 13, 2020 (10 pages).
International Searching Authority, Search Report and Written Opinion issued in International Application No. PCT/SE2018/050500, dated Oct. 23, 2019 (12 pages).
International Searching Authority, Written Opinion issued in International Application No. PCT/SE2018/050500, dated Jan. 9, 2020 (4 pages).
International Searching Authority, Written Opinion issued in International Application No. PCT/SE2018/050500, dated Mar. 13, 2020 (5 pages).
International Searching Authority, International Preliminary Report on Patentability issued in International Application No. PCT/SE2018/050500, dated Jun. 19, 2020 (14 pages).
Chinese Patent Office, First Office Action issued in CN 201880093198.9, dated Apr. 12, 2021 with English Translation (20 pages).
Russian Patent Office, Office Action issued in RU Application No. 2020141044, dated Jun. 1, 2021 with English Translation (19 pages).

* cited by examiner

FIBROUS PRODUCT

CROSS-REFERENCE TO RELATED APPLICATION

This application is a national phase entry of, and claims priority to, International Application No. PCT/SE2018/050500, filed May 15, 2018. The above-mentioned patent application is incorporated herein by reference in its entirety.

TECHNICAL FIELD

This application is related to fibrous products, such as tissue paper and non-woven products.

BACKGROUND

Tissue paper or nonwoven products may be used for different purposes, such as for facial cleaning, e.g., wiping of the nose or wiping the face with the aim of cleaning it, or for drying hands. An important property for such a tissue paper or nonwoven is the ability to efficiently clean and dry while at the same time keeping the skin healthy and unimpaired.

Tissue paper and nonwoven may be abrasive to the skin and cause discomfort upon use. This problem is particularly pronounced in situations in which the tissue paper or nonwoven is used frequently for blowing the nose or upon after handwashing. The latter situation is common, for example, for staff at hospitals or at food-preparation establishments when handling food.

Thus, there is a need for a tissue paper or nonwoven exhibiting both increased softness and comfort properties, as well as increased hygiene and skin health properties.

SUMMARY

In order to achieve these technical objectives, this application is directed to a fibrous product including a fibrous material, in which the fibrous material comprises lactic acid and/or a salt thereof in an amount of, per ply provided with lactic acid, in the range of from about 0.1 to about 15 $g/m^2$, such as from about 0.3 g to about 10 $g/m^2$, from about 0.3 to about 5 $g/m^2$, from about 0.5 to about 5 $g/m^2$, from about 1.0 to about 3.0 $g/m^2$, from about 1.0 to about 2.5 $g/m^2$, from about 1.0 to about 2.0 $g/m^2$, or from about 1.0 to about 1.5 $g/m^2$. The water activity of the fibrous product is typically from about 0.03 to about 0.85, such as from about 0.05 to about 0.85, from about 0.1 to about 0.85, from about 0.03 to about 0.75, from about 0.05 to about 0.75, from about 0.1 to about 0.75, from about 0.03 to about 0.65, from about 0.05 to about 0.65 or from about 0.1 to about 0.65. The salt of lactic acid may, for example, be sodium lactate, potassium lactate and/or calcium lactate.

In one embodiment, the fibrous material in the fibrous product disclosed herein may further comprise one or more pH regulating substances, such as NaOH or KOH.

In another embodiment, the fibrous product may for example and without limitation, be in the form a hand towel, handkerchief, facials, dry wipe, napkin, washcloth, cleaning cloth, house hold towel, wiping tissue or toilet paper.

In yet another embodiment, the fibrous product may also for example be in the form of a tissue paper product, a nonwoven product or a mixed tissue paper and nonwoven product.

In some embodiments, the fibrous product may have a pH of about 6.5 or less, such as a pH of from about 2.5 to about 6.5, from about 3.0 to about 6.0, from about 3.0 to about 5.5, from about 3.0 to about 5.0, from about 3.0 to about 4.5, from about 3.0 to about 4.0, or from about 3.0 to about 3.5.

In further embodiments, the fibrous product may have an increase in flexibility of at least about 10%, measured as the D-value, when compared to the same fibrous material without lactic acid and/or a salt thereof.

In one embodiment, the lactic acid and/or a salt thereof is provided to at least one of the outer surfaces of the fibrous product.

In another embodiment, the fibrous product may be a multi-ply or a one-ply (single-ply) product.

This application is also directed to a method for producing a fibrous product comprising a fibrous material, and in which the fibrous material includes lactic acid and/or a salt thereof in an amount of from about 0.1 to about 15 $g/m^2$, such as from about 0.3 g to about 10 $g/m^2$, from about 0.3 to about 5 $g/m^2$, from about 0.5 to about 5 $g/m^2$, from about 1.0 to about 3.0 $g/m^2$, from about 1.0 to about 2.5 $g/m^2$, from about 1.0 to about 2.0 $g/m^2$, or from about 1.0 to about 1.5 $g/m^2$, and in which the fibrous product has a water activity of about 0.85 or less. The method includes (a) providing a fibrous material; (b) providing a composition comprising lactic acid and/or a salt thereof to the fibrous material, in which the composition comprises lactic acid and/or a salt thereof and (c) drying the fibrous material provided with the composition comprising lactic acid and/or a salt thereof to thereby provide a fibrous product.

In one embodiment, the composition comprising lactic acid and/or a salt thereof may be provided to the fibrous material by coating, such as by slot-dye coating, printing, roll coating or spraying. The drying of the fibrous material may be performed by air drying or infrared ("IR") drying.

The method disclosed herein for producing a fibrous product may be used for producing the fibrous product disclosed herein. This application is therefore also directed to a fibrous product obtainable or obtained by the method disclosed herein.

In step (b) of the method for producing a fibrous product, the composition includes lactic acid and/or a salt thereof is provided to at least one of the outer surfaces of the fibrous product.

This application is also directed to the use of lactic acid and/or a salt thereof for improving the softness of a fibrous material. Typically the fibrous material after treatment with lactic acid and/or a salt thereof has a flexibility increase, measured as the D-value (see TSA measurements in Table 4 below), of at least about 10%, when compared to the same fibrous material but without lactic acid and/or a salt thereof.

This application also discloses the use of the fibrous product disclosed herein for reducing the pH of the skin of a user of the fibrous product, such as for reducing the skin pH by at least about 0.5 pH units.

This application also discloses a method for improving the softness of a fibrous material, the method including: (a) providing a fibrous material; (b) providing a composition comprising lactic acid and/or a salt thereof to the fibrous material; and (c) drying the fibrous material to a water activity of about 0.85 or less to thereby provide a fibrous product having an improved softness.

The fibrous material may thereafter have a flexibility increase, measured as the D-value (see TSA measurements in the below), of at least about 10%, when compared to the same fibrous material but without lactic acid and/or a salt thereof.

Definitions

As used herein the terms "tissue paper product" and "nonwoven product" refer to a fibrous material provided with a dry coating that comprises lactic acid and/or a salt thereof.

As used herein, the term "fibrous material" refers to a "tissue paper material" or a "nonwoven material" in which the fibers and/or filaments are held together by papermaking bonds, bonding agents, mechanical entangling and/or thermobonding, as more fully described below, which has not been provided with a dry coating comprising lactic acid and/or a salt thereof. Thus the term "tissue paper material" refers both to wetformed, airlaid, and foam-formed tissue paper materials. Examples of "nonwoven material" are spunlaced materials, thermobonded fibrous materials, spunbond material, and meltblown materials.

As used herein, the term "dry coating" and the like refer to a coating being formed on a web material by application of a composition in a liquid carrier that is liquid at a temperature of 15-50° C., such as at room temperature, such as an aqueous solution, followed by drying of the web material, thereby resulting in a dry coating formed on the web material. A dry coating, as referred to herein, relates to a coating that has a water content not significantly exceeding the level of water being inevitably present due to an equilibrium between the coating and the surrounding atmosphere. "dry coating" in the context of this application is therefore intended to mean a coating formed on a fibrous material after providing a composition comprising lactic acid and/or a salt thereof to the fibrous material and drying the fibrous material provided with the composition comprising lactic acid and/or a salt thereof.

As used herein, the term "lactic acid" refers to a compound having the chemical formula $CH_3CH(OH)COOH$. Both the D and the L form of lactic acid, or a mixture thereof with different ratios of the D and L form, may be used in the context of this application. The term "a salt thereof" is intended to mean a salt of lactic acid, such as sodium lactate, potassium lactate or calcium lactate.

As used herein, the terms "buffered", "buffering" and the like are intended to mean a salt of a weak acid (or base) that is blended with the acid and used for securing a stable and evenly distributed pH of the treated material. In accordance with this application, such a weak acid may be an alkali metal salt of lactic acid, such as sodium lactate, potassium lactate or calcium lactate, which may be used instead of or in addition to lactic acid.

Water activity is the ratio of the vapor pressure of water in a material (p) to the vapor pressure of pure water ($p_0$), at the same temperature. Water activity may be useful for predicting microbial, but also chemical and physical, stability of a product. One method for determining water activity is the dew point method, which is described in further detail below.

BRIEF DESCRIPTION OF THE DRAWINGS

The features and advantages of the invention will be appreciated upon reference to the following drawings. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

Fibrous Product

This application discloses a fibrous product including lactic acid and/or a salt thereof. The present inventors surprisingly found that the addition of lactic acid and/or a salt thereof to a fibrous material resulted in a softening of the fibrous material, thus enabling providing a fibrous product that is gentler to the skin, leading to a reduced risk for damaging the skin and/or causing of discomfort upon use of the fibrous product.

Use of the fibrous product disclosed herein may therefore reduce the negative effects, such as skin irritation, formation of small wounds/incisions, and/or lowering (damage) the skin's barrier functions, which may arise upon use of regular fibrous materials. The fibrous product disclosed herein thus has skin caring properties. Further, the fibrous product disclosed herein may be more comfortable to use due to its softness. These features give a fibrous product with skin care properties, in particular, for frequent users and people with sensitive skin.

The fibrous product disclosed herein thus has an improved softness and skin caring properties as compared to regular fibrous materials.

As explained more fully below, the fibrous product may have a D-value that is at least about 10% higher than the D-value of a fibrous material that does not comprise lactic acid. The fibrous product may thus have a flexibility increase of at least about 10%, measured as the D-value, when compared to the same fibrous material but which does not comprise lactic acid and/or a salt thereof. The D-value may be measured using a Tissue Softness Analyzer (such as available form Emtec, of Germany) and according to the method disclosed in further detail below.

This application is therefore directed to a fibrous product comprising a fibrous material, in which that fibrous material comprises lactic acid and/or a salt thereof in an amount of from about 0.1 to about 15 $g/m^2$, such as from about 0.3 g to about 10 $g/m^2$, from about 0.3 to about 5 $g/m^2$, from about 0.5 to about 5 $g/m^2$, from about 1.0 to about 3.0 $g/m^2$, from about 1.0 to about 2.5 $g/m^2$, from about 1.0 to about 2.0 $g/m^2$, or from about 1.0 to about 1.5 $g/m^2$ wherein said fibrous product has a water activity of about 0.85 or less. The lactic acid and/or a salt thereof may be provided as a coating onto a fibrous material. These amounts of lactic acid refer to the amount per ply of fibrous material provided with lactic acid, i.e. per outer surface (outer ply) of the fibrous product.

The pH of healthy skin is generally and naturally below 5 (Natural skin surface pH is on average below 5, which is beneficial for its resident flora, International Journal of Cosmetic Science, 2006, 28, 359-370, H. Lambers et. al). A higher skin pH has been linked to a decreased barrier function, decreased moisturization and increased scaling. The effect of pH on adhesion of resident skin microflora has also been assessed and it has been shown that an acidic skin pH (4-4.5) keeps the resident bacterial flora attached to the skin, whereas an alkaline pH (8-9), promotes dispersal from the skin; see e.g. Natural skin surface pH is on average below 5, which is beneficial for its resident flora, International Journal of Cosmetic Science, 2006, 28, 359-370, H. Lambers et. al) Lactic acid is a substance already naturally present on the skin.

Fibrous materials may typically have a pH of 6-8. As is discussed in the experimental section below, by using the fibrous product disclosed herein, it is possible to lower the pH of the skin. Thus, the fibrous product disclosed herein may be used for improving the skin's barrier function by lowering the skin's pH.

The fibrous product according to this application has a pH of about 6.5 or less, such as a pH of about 2.5 to about 6.5, from about 3.0 to about 6.0, from about 3.0 to about 5.5, from about 3.0 to about 5.0, from about 3.0 to about 4.5, from about 3.0 to about 4.0, or from about 3.0 to about 3.5. A pH for the fibrous product of about 4 has proven advantageous to maintain a natural skin pH and thus promotes skin health. The lower limit for the pH of the fibrous product is set by the pH value at which no benefit is provided to the skin. A pH below 3 may be less desirable insofar as no benefit is provided to the skin at that pH level. Thus, the fibrous product typically has a pH of from about 3 to about 5. The pH of the fibrous product can be measured by measuring the pH of the fibrous product in a wet condition by first submerging it in water, or saline, before measuring the pH, as disclosed below in Example 4. The pH of the fibrous product can also be measured by using a surface electrode (see Example 4).

In order to prepare a composition comprising lactic acid and/or a salt thereof, lactic acid and/or a salt thereof may be dissolved in an aqueous solution, or in water. The pH of the composition comprising lactic acid and/or a salt thereof may be regulated with a lactic acid salt, such as a sodium or potassium salt of lactic acid, and/or another pH regulating substance, such as a hydroxide, such as KOH or NaOH.

The fibrous product is a dry product, i.e. a product which has a water activity of about 0.85 or less. Typically, the coating of lactic acid and/or a salt thereof has a water content not significantly exceeding the level of water being inevitably present due to equilibrium between the coating and the surrounding atmosphere. The fibrous product therefore typically has a water activity of from about 0.03 to about 0.85, such as from about 0.05 to about 0.85, from about 0.1 to about 0.85, from about 0.03 to about 0.75, from about 0.05 to about 0.75, from about 0.1 to about 0.75, from about 0.03 to about 0.65, from about 0.05 to about 0.65 or from about 0.1 to about 0.65. Water activity is measured by standard techniques for measuring water activity of fibrous materials. A commonly used method for measuring water activity of a sample is to use the dew point method. The dew point method uses a sealed temperature controlled chamber. The sample is placed in the chamber and sealed. The free water is allowed to escape into the air in the chamber. It remains there until all the free water has left the sample (a condition of equilibrium). At equilibrium the relative humidity of the air in the chamber is measured. The relation of this reading to pure water is the water activity measurement expressed as the term aw. The range of water activity is from zero (no free water) to 1.0 (pure water).

The fibrous product may include lactic acid and/or a salt thereof. This means that the fibrous material may be provided with only lactic acid, a mixture of lactic acid and/or one or more lactic acid salts, or one or more lactic acid salts. Examples of lactic acid salts include, but are not limited to sodium lactate, potassium lactate, and/or calcium lactate. Further, in order to regulate the pH of the composition comprising lactic acid and/or a salt thereof used for preparing the fibrous product, the composition may comprise one or more pH regulating substances such as a hydroxide, e.g. KOH or NaOH, which will then also be present on the final fibrous product.

In addition to the lactic acid and/or a salt thereof, one or more other substances can be added to the fibrous material to provide additional skin comfort and health benefits. Examples of such additives are botanical actives and oils, such as panthenol, glycerol, other organic acids, surfactants, vitamin, and/or antimicrobial substances. Other examples of such additives include, but are not limited to, one or more of a substance selected from the group consisting of surfactants skin caring agents, rehydrating substances, smoothening substances, antimicrobial substances, bacteriostatic substances-catching agents, microfibrillated cellulose (MFC), and release controlling agents. Further, perfume may be added to the fibrous material. The additives may be provided in the composition comprising lactic acid and/or a salt thereof or separately to the fibrous material.

Fibrous products according to this application are typically fibrous products intended for skin contact. Examples of fibrous products according to this application are hand towels, handkerchiefs, facials, dry wipes, napkins, washcloths, cleaning cloths, household towels, wiping tissues and toilet papers.

The fibrous product according to this application may comprise a combination of different fibrous materials or only one kind of fibrous material. The fibrous product may thus for example be a tissue paper product, a nonwoven product or a mixed tissue paper and nonwoven product, i.e. a fibrous product in which the fibrous material is tissue paper, nonwoven or a combination of tissue paper and nonwoven.

The fibrous product may be a one-ply or multiply product comprising two or more plies, such as two, three, four, five or six plies.

The lactic acid and/or a salt thereof may be present on one or more of the outer surfaces (sides) of the fibrous material. If a multi-ply fibrous material is used, the lactic acid and/or a salt thereof may be present on one or more of the outer surfaces, but typically not on the surfaces facing the inside of the product. Thus, when preparing the fibrous product, the lactic acid and/or salt thereof is typically only provided to the outer plies and only on the outer surface of these plies. For both a multi-ply and a one-ply product, the lactic acid and/or a salt thereof may be provided to only one of the surfaces of the product facing the outside. Typically, the lactic acid and/or a salt thereof is at least provided to the surface that is intended to be in contact with a user of the fibrous product. The lactic acid and/or a salt thereof typically forms a coating on the surface to which it is applied, although some of the lactic acid and/or a salt thereof provided to a fibrous material may be absorbed into the fibrous material.

According to this application, the lactic acid and/or a salt thereof is typically not provided via an adhesive used for binding tissue paper web plies together in a two or multi-ply fibrous product.

This application is also directed to the use of lactic acid and/or a salt thereof for improving the softness of a fibrous material.

Typically, the flexibility, measured as an increase in the D-value, of a fibrous product described herein is at least about 10% higher when compared to an untreated fibrous material. Typically, the softness, measured as a decrease in the TS7-value, of a fibrous product of the type described herein is at least about 15% lower, such as about 20% or about 25% lower, as compared to an untreated fibrous material.

This application is also directed to the use of a fibrous product as defined herein for reducing the pH of the skin of a user of that fibrous product. Typically, the skin pH is reduced by a factor of at least about 0.5 pH units, on the part of the skin that is wiped with the fibrous product, when the fibrous product is used.

Production of the Fibrous Product

The lactic acid and/or a salt thereof may be provided to the fibrous material by the application of a composition which typically is a solution or an emulsion comprising lactic acid and/or a salt thereof to that fibrous material. As more fully explained below, the lactic acid and/or a salt thereof is typically added at least to the outer surface(s) of the fibrous product that is intended to be in contact with a user of that product.

This application thus discloses a method for producing a fibrous product, such as a fibrous product as disclosed herein, comprising a fibrous material in which the fibrous material comprises lactic acid and/or a salt thereof in an amount of from about 0.1 to about 15 $g/m^2$, such as from about 0.3 g to about 10 $g/m^2$, from about 0.3 to about 5 $g/m^2$, from about 0.5 to about 5 $g/m^2$, from about 1.0 to about 3.0 $g/m^2$, from about 1.0 to about 2.5 $g/m^2$, from about 1.0 to about 2.0 $g/m^2$, or from about 1.0 to about 1.5 $g/m^2$, and wherein said fibrous product has a water activity of about 0.85 or less. The method includes: (a) providing a fibrous material; (b) providing a composition comprising lactic acid and/or a salt thereof to the fibrous material; and (c) drying the fibrous material provided with the composition comprising lactic acid and/or a salt thereof to provide a fibrous product.

The fibrous product produced may be a fibrous product as disclosed in further detail below.

The composition comprising lactic acid and/or a salt thereof is typically prepared by dissolving the lactic acid and/or a salt thereof in a carrier which is liquid at room temperature, optionally followed by regulating the pH thereof by using for example, a lactic acid salt and/or a hydroxide, such as KOH or NaOH. The liquid carrier may be an aqueous solution, glycerol or ethanol or a combination of one or more of these, for example. The liquid carrier may comprise ethanol and/or other polar organic solvents. Further, the composition comprising lactic acid and/or a salt thereof may comprise one or more of an additive, such as botanical actives and oils, such as panthenol, glycerol, other organic acids, surfactants, vitamin, and/or antimicrobial substances. Other examples of such additives include, but are not limited to, one or more of a substance selected from the group consisting of surfactants skin caring agents, rehydrating substances, smoothening substances, antimicrobial substances, bacteriostatic substances-catching agents, microfibrillated cellulose (MFC), and release controlling agents. Further, the composition comprising lactic acid and/or a salt thereof may comprise perfume.

The concentration of lactic acid and/or a salt thereof in the composition applied to the fibrous material is typically from about 2 to about 85 wt %, such as from about 40 to about 85 wt %, in particular when the lactic acid is present in an aqueous solution.

The composition comprising lactic acid and/or salt thereof is typically added to the fibrous material in the converting process, during the transformation from base material into finished products. The composition comprising lactic acid and/or a salt thereof is then typically added with a suitably chosen coating technique as described herein on dry material.

As used herein, the term "dry coating" refers to a coating being formed on a material by application of a composition comprising, at room temperature, a liquid carrier, such as water, comprising lactic acid and/or a salt thereof, followed by drying of the material, thereby resulting in a coating formed on the material. The coating formed has a water content not significantly exceeding the level of water being inevitably present due to equilibrium between the coating and the surrounding atmosphere. Typically, the water activity of the tissue paper product and/or nonwoven product is about 0.85 or less as more fully below. The composition comprising lactic acid and/or a salt thereof may be provided to the fibrous material by any suitable method for coating, including, but not limited to, by slot dye coating, printing, roll coating or spraying.

The composition comprising lactic acid and/or a salt thereof is provided to the fibrous material so that a coating is formed on at least one of the fibrous product's outer surfaces. In a multi-ply product one or more of the plies may be coated with the lactic acid and/or a salt thereof. The coating may essentially be as a layer around at least part of the circumference of the individual fibers but the lactic acid may also to some extent be absorbed into the fibers.

The composition comprising lactic acid and/or a salt thereof may be essentially homogenously applied on the fibrous material, or may be applied in a patterned manner, covering only part of the surface on which it is applied. When applied in a patterned manner, the coating formed may for example cover at least about 10 area-%, such as from about 10 to about 90 area-% of the ply on which the coating is applied. For example, the coating may be applied regionally to parts of a fibrous material that is intended to be in contact with skin.

The drying step, step (c) may be carried out by e.g. heated cylinder, air drying, IR drying or another drying method.

The fibrous product produced may be a fibrous product of the type disclosed herein. This application is therefore also directed to a fibrous product obtainable or obtained by the method disclosed herein.

This application is also directed to a method for improving the softness of a fibrous material, the method comprising: a) providing a fibrous material; b) providing a composition comprising lactic acid and/or a salt thereof to the fibrous material; and c) drying the fibrous material to a water activity of about 0.85 or less to thereby provide a fibrous product having an improved softness.

In the method for improving the softness of a fibrous material, the method steps may be carried out as disclosed above for the method for producing a fibrous product comprising a fibrous material in which the fibrous material comprises lactic acid and/or a salt thereof in an amount of from about 0.1 to about 15 $g/m^2$, and in which the fibrous product has a water activity of about 0.85 or less.

Fibrous Materials

In accordance with this application, a fibrous material is treated with lactic acid and/or a salt thereof. The fibrous material may be, for example, a "tissue paper material" or a "nonwoven material" in which the fibers and/or filaments are held together by papermaking bonds, bonding agents, mechanical entangling and/or thermobonding.

Tissue Paper Material

The term "tissue paper" as used herein covers the base (raw) tissue paper ("tissue paper web") in the form obtained from a tissue paper machine, as well as one-ply or multi-ply final products ("tissue paper products") made of base tissue, and tailored to the end user's needs by further converting steps.

A "tissue paper web" may be a one-ply base tissue in the form obtained from a tissue machine. The tissue paper web is a sheet of paper made by a process comprising the steps of: forming an aqueous suspension of pulp fibers i.e., the so-called "furnish", depositing the aqueous suspension onto a wire to form a wet web, dewatering, drying, and creping the web.

The tissue paper web may have a basis weight of from about 8 to about 50 $g/m^2$, in particular from about 10 to about 30 $g/m^2$, more particularly from about 12 to about 25 $g/m^2$.

The tissue paper web is composed of one or more layers (i.e., a single-layered web or a multi-layered web). The term "layer" refers to a stratum within the web having a defined fiber composition. The one or more layers is/are formed by depositing one or more streams of pulp furnishes onto a wire with a pressurized single- or multi-layered headbox. This technique is well-known to those skilled in the art. It renders possible the use of different kinds of fibers in each layer of the web. The "multi-layered" tissue paper web may have 2 to 5 layers, and more specifically 2 or 3 layers.

The term "ply" as used herein refers to the one or more plies of tissue paper in the final tissue paper product as are obtained after processing ("converting") one or more base tissue paper webs. Each individual ply consists of a tissue paper web comprising one or more layers, e.g. one, two, three, four or five layers.

Based on the underlying compatibility of the production processes (wet forming), "tissue" production is counted among the papermaking techniques. The production of tissue is distinguished from paper production by its relatively low basis weight and its much higher tensile energy absorption index.

The tensile energy absorption index is arrived at from the tensile energy absorption in which the tensile energy absorption is related to the test sample volume before inspection (length, width, thickness of sample between the clamps before tensile load). Paper and tissue paper also differ in general with regard to the modulus of elasticity that characterizes the stress-strain properties of these planar products as a material parameter.

A tissue's high tensile energy absorption index results from the outer or inner creping. The former is produced by compression of the paper web adhering to a cylinder as a result of the action of a crepe doctor or in the latter instance as a result of a difference in speed between two wires ("fabrics"). This causes the still moist, plastically deformable paper web to be internally broken up by compression and shearing, thereby rendering it more stretchable under load than an uncreped paper. A high tensile energy absorption index can also be achieved by imparting to the tissue a 3D structure by the wires themselves. Most of the functional properties typical of tissue and tissue products result from the high tensile energy absorption index (see EN 12625-4 and EN 12625-5).

Typical properties of tissue paper include the ready ability to absorb tensile stress energy, their drapability, good textile-like flexibility, properties which are frequently referred to as bulk softness, a high surface softness, a high specific volume with a perceptible thickness, as high a liquid absorbency as possible and, depending on the application, a suitable wet and dry strength as well as an interesting visual appearance of the outer product surface. These properties allow tissue paper to be used, for example, as cleaning cloths (e.g., household towels), sanitary products (e.g. toilet paper and hand towels), paper handkerchiefs, cosmetic wipes (facial tissues) or as serviettes/napkins.

The "pulp fibers" used in embodiments disclosed herein are selected from chemical pulp fibers, mechanical pulp fibers subjected to a chemical pretreatment recycled fibers or a mixture thereof.

"Chemical pulps" are, according to DIN 6730, fibrous materials obtained from plant raw materials of which most non-cellulosic components have been removed by chemical pulping without substantial mechanical post treatment, such as Kraft pulp.

In contemplated embodiments, use can also be made of mechanical pulps subjected to chemical pre-treatment, such as chemo-mechanical pulp ("CMP pulp"), or chemo-thermo-mechanical pulp ("CTMP pulp").

As "hardwood fibers" we understand fibrous pulp derived from the woody substance of deciduous trees (angiosperms). Typically, hardwood fibers are "short" fibers having a length of from about 0.5 to about 2 mm, such as from about 0.5 to about 1.5 mm, a diameter of from about 15 to about 30 μm and a wall thickness of from about 2 to about 3 μm. Hardwood such as *Eucalyptus* is normally pulped by a Kraft process.

Suitable hardwood fibers for use in embodiments disclosed herein may originate from *eucalyptus*, beech, aspen, acacia and birch, and more specifically from *eucalyptus*.

As "softwood fibers" we understand fibrous pulp derived from the woody substance of coniferous trees (gymnosperms). Typically, softwood fibers are "long" fibers having a length of from about 2 to about 4 mm, such as from about 3 to about 4 mm, a diameter of from about 30 to about 40 μm, and a wall thickness of from about 3 to about 4 μm. They are normally pulped by the Kraft process.

Suitable softwood fibers for use in embodiments disclosed herein may originate from pine, spruce, red cedar, douglas fir, hemlock, or larch. More specifically, suitable softwood fibers for use in the embodiments disclosed herein are Northern Bleached Softwood Kraft (NBSK) fibers. In specific embodiments at least part of the NBSK fibers to be used is refined, such as to a degree of fineness of from about 19 to about 35° SR, and more specifically from about 19 to about 26° SR.

As "non-wood fibers" we understand fibrous pulp derived from the non-woody substance of plants such as cotton, kapok, milkweed, bamboo, bagasse, hemp, linen, sisal, abaca, pineapple, jute, kenaf, straw, flax or miscanthus.

Nonwoven Material

Nonwoven has a general definition that can be found in ISO 9092:2011.

The nonwoven web can be drylaid, either carded or airlaid, wetlaid or produced in-situ, i.e. direct-laid (meltblown or spunlaid). These formation processes can also be combined in a wide variety of possibilities, e.g. a drylaid staple fiber web can be covered with an airlaid layer, a meltblown can be mixed with a stream of airlaid pulp (the Coform process), spunlaid and meltblown can be mixed in up to 5-7 layers typically having meltblown as mid-layer(s).

After the nonwoven web formation, the material needs to undergo a bonding step to give the material enough strength and coherent properties to be suitable for its intended end use. Bonding can be made in several different ways, either by mechanical action (needle punching or hydroentanglement), adding heat to thermoplastic fibers making them [partially] melt (through air bonding with hot air or mechanically by heated rollers in contact with the web) or by chemical means (coating, printing or spraying of a binder, e.g. latex).

After the bonding the web may be subjected to a post treatment to enhance either visual, tactile or functional performance. The post treatment can be a printing process to make the material visually appealing or to add a performance enhancer to the material (such as e.g. abrasiveness) or it can be a dry-creping process (a so called Micrex process) to enhance apparent thickness and increase foldability and softness.

Raw materials to nonwovens can be either man-made or natural.

Suitable fibers for drylaid carded nonwovens are staple fibers typically around 38-45 mm and around 1.7 dtex. Man-made staple fibers can either be made from thermoplastic polymers, such as polypropylene, or polyesters, such as polylactides and polyethyleneterephthalate, or polyamides. Other suitable man-made fibers are those made from cellulose-derived such as rayon or lyocell. Natural fibers can for example be cotton, flax, ramie or any other suitable natural source. Natural fibers will have a wider fiber length distribution than man-made fibers.

Raw materials for airlaid nonwovens are typically natural cellulose fibers, i.e. pulp fibers, with typical lengths 2-4 mm. Thermoplastic polymers with short fiber lengths (typically <6 mm) can also be used, especially if the material is to be through air bonded with hot air. In such circumstance the thermoplastic fibers might me made of two separate polymers, the inner part having higher melting point than the outer shell. The lower melting temperature in the shell will allow the fibers to create thermal bonding and by this increase the coherent properties on the nonwoven. This kind of fibers are called bicomponent fibers.

For wetlaid nonwovens the fibers need to be shorter to allow a good fiber dispersion and an even material formation. The wet modulus will also be of importance when wetlaying nonwovens. Fibers with very low wet modulus, such as cotton, might be difficult to wet form. Typical fiber lengths are <12 mm.

For in-situ produced nonwovens the raw material may be any thermoplastic polymer of natural or manmade origin with enough coherent properties to allow to be drawn into continuous thin filaments (typically 10-20 μm). Raw materials might be selected from the group of polyolefins, such as polypropylene or polyesters, such as polylactides and polyethyleneterephthalate, or polyamides. Copolymers of these polymers may be also used.

Softness Test Method—TSA Method

Softness, smoothness and stiffness properties of different sheet materials may be analyzed with a softness test method (TSA—Tissue Softness Analyzer), a method that uses acoustic waves and has demonstrated to correlate well with hand panel tests for thin materials like tissue or nonwoven. The softness test method has therefore been used for determining suitable softness, smoothness and stiffness of a tissue or nonwoven material.

The test method follows the general outline of the TSA instrument manual dated 2013 Jul. 8 (Collection of the TSA Operating Instruction, Multi Functional Measuring System, Tissue Softness Analyzer, 2012 Dec. 12, available from Emtec electronic GmbH (Gorkistrasse 31; D-04347 Leipzig Germany) with the settings or modifications as set forth therein or below.

Technical Basics of TSA

The hand feel of a fibrous material is affected by components at various levels; from the polymers at a molecular level to the fibrous network at a macro level. Stiffness of individual fibers, internal structure, fiber-to-fiber bond strength, softener chemicals, etc. all affect the hand feel, but so do any mechanical treatment to which the web material is subjected, such as creping, and embossing. The TSA analysis can measure the effects of material differences at various levels.

Measuring Principle

The sample will be fixed in a measuring cell like a drumhead. Below is placed a vibration sensor, above is placed a vertical movable measuring head with a rotating blade that is pushed onto the sample with a defined load. In step 1 of the procedure, a rotation with defined speed is executed. The motion of the blades over the sample generates different types of vibrations/noise, which is detected with a vibration sensor. In step 2 of the procedure, the sample is deformed perpendicular to the surface to measure elastic, visco-elastic and plastic properties.

Evaluation

The resulting vibrations/noise spectrum from step 1 of the measurement is an overlapping of two single spectra; (a) Vertical vibration of the sample like a membrane and (b) Excitation of horizontal vibrations of the blades itself caused by momentary blocking and swinging back of the blades by the fibers when moving over the surface.

In step 2 of the measurement the rotor applies a defined load in three cycles in a vertical direction onto the sample, the load (F) being 0 mN, 100 mN and constant of 600 mN. Reference is made to the Emtec manual for further details of the measuring principle. The measured D—stiffness correlates with the stiffness of the material. A low D value corresponds to a stiffer material at the same time as a higher value corresponds to a more flexible and textile like material.

Thus, the method results in three parameters, namely TS7—softness, TS750—smoothness and D—stiffness, as defined in TSA Operating Instructions 2013 Jul. 8 (Multi Functional Measuring System, Tissue Softness Analyzer). The parameters are all of relevance for evaluating whether an article may possess a soft and cloth-like feeling to a wearer. A high value of D and low values of TS7 and TS750 have shown to correspond to the provision of a desired soft material as touched upon by a human hand.

Apparatus, Materials and Conditions

As mentioned above, the test follows the general outline of the TSA instrument manual dated 2013 Jul. 8 (Multi Functional Measuring System, Tissue Softness Analyzer) that is available from Emtec electronic GmbH (Gorkistrasse 31; D-04347 Leipzig Germany) with the settings or modifications as set forth therein or herein.

A Tissue Soft Analyzer (TSA) from Emtec electronic GmbH (TSA Tissue Softness Analyzer, model B458; UC version 1.72, Serie no.: 04-14-32; Software: Emtec 3.18 13-ems-143; Hard Ware: 2.4 and Windows 7 Enterprise Service pack 1) was used in the measurements according to the method.

The Sample diameter was 112.8 mm, the tested diameter was about 70 mm, and the standard rotor (about 59 mm in diameter) of the instrument was used at a rotation speed of 2 RPS.

The Softness resonance frequency peak of the measurements was 6,500 Hz. All measurements and calibrations were performed at standard climatic conditions of 23° C. (±1° C.) and 50% r.H. (±5%) in general following ISO DIN EN 20187.

The TSA is equipped with a balance for determination of grammage and thickness (gravimetric) of the samples in accordance with ISO 12625-6:2005.

The principle for TSA measurement is outlined in TSA Operating Instruction No. 12, Collection of the TSA Operating Instruction, Multi Functional Measuring System, Tissue Softness Analyzer, 2012 Dec. 12, available from Emtec electronic GmbH (Gorkistrasse 31; D-04347 Leipzig Germany).

EXPERIMENTAL SECTION

Example 1: Preparation of Lactic Acid Buffer Solution

Buffer 1: Lactic Acid Buffer pH 3 (4 M) 500 ml 15.8 g (86.1%) Potassium hydroxide was weighed in, in a volumetric flask (500 ml). Approximately 100 ml de-ionized water was added and the flask was swirled until the potassium hydroxide was completely dissolved. 176 ml of 85% lactic acid in water was then added and the flask was again carefully swirled to mix the solution. Approximately 250 ml water was then added and pH value of the solution was determined. If necessary, pH was adjusted to target pH 3, using hydrochloric acid or potassium hydroxide, before filling up the volumetric flask to the 500 ml mark.

Buffer 2: Lactic Acid Buffer pH 3 (9 M) 500 ml 37 g (97%) Sodium hydroxide was weighed in, in a volumetric flask (500 ml). Thereafter, 90 g de-ionized water was added. Finally, the Lactic acid (85%) was carefully added in small portions, during stirring, up to a volume of 500 ml. When all the solid Sodium hydroxide was dissolved, a small portion of liquid was removed from the volumetric flask and pH was measure. The flask was filled up with de-ionized water and if needed, the pH was adjusted to target pH 3.

Buffer Printing Pilot Scale

Buffer 3: Lactic Acid Buffer pH3 (4 M) 10 Liter

For practical reasons, a larger amount of lactic acid buffer was prepared before the printing trial. The recipe above for Buffer 1, was then scaled up to a final volume of 10 liter by using 3520 ml lactic acid (85%) and 316 g KOH (86.1%).

Example 2: Tissue Surface Treatment, Spray Application

The lactic acid buffer solution prepared according to Buffer 1 and Buffer 2 in Example 1 was applied on tissue through spray application. An untreated tissue sheet of defined size was weighed in dry condition (ATMOS 2-ply 41 gsm or TAD 39 g/m$^2$, 100% virgin fibers). The dry tissue sheet was then attached on a vertically net supporting a fume hood. The sheet was thereafter sprayed with different amounts of lactic acid buffer solution. The spraying was manually done in a repeatable pattern that covered the whole tissue surface. The amount of applied buffer was adjusted with the nozzle on the spraying equipment. Immediately after spraying, the wet weight was noted and the sheet was thereafter dried in room temperature for at least 24 hours.

Example 3: Tissue Surface Treatment, Printing in Pilot Scale

Lactic acid buffer solution prepared according to Buffer 3 in Example 1 was applied onto the tissue surface using the anilox printing technique with full phase coverage. The substrate was ATMOS single-ply 20.5 g/m$^2$ (100% virgin fibers). It was delivered as two mother rolls, each having a width of 60 cm. Single-ply ATMOS tissue was printed on the front side on a roll-to-roll converting machine for tissue. The machine was operated at 50 m/min. The machine comprised of a de-winding station, a print station for applying the buffer solution, an infrared dryer and a rewinding station for the treated tissue web. The print station was configured with a smooth anilox roll, a smooth rubber transfer roll, and a steel counter roll. The tissue passed through the nip between the transfer roll and the counter roll and printing was done on the front side of the ATMOS substrate.

The wet coat weight was adjusted by the relative rotation speed of the anilox roll. The wet coat weight was verified gravimetrically by monitoring the weight loss per minute from the reservoir with buffer solution. The wet coat weight was calculated assuming 100% transfer of buffer solution from the anilox to the tissue. The coating was done at three levels (0.5, 1.5 or 2.5 g/m$^2$) and the actual amount of applied buffer solution were later confirmed by Ion chromatography. Samples of printed 1-ply base tissue were taken out of analysis. In a separate lamination step, the base tissue was converted into a 2-ply product. Base tissue, with the treated surfaces facing outwards, was laminated with polyvinyl alcohol glue and embossed with blue colored pattern. The final product thus consisted of two plies with the lactic acid treatment on the outer surfaces. The 2-ply converted tissue was later cut by hand and samples were taken out for analysis.

Example 4: pH Measurement on Tissue Paper

The pH value of the lactic acid-treated tissue, produced accordingly Example 3, was determined with two different methods. 1. Surface pH flat electrode 2. Extracted pH ISO 6588-1 (without KCl)

Method 1—Surface pH flat electrode: Tissue material was cut in small pieces 5×5 cm. A material piece was placed on a plate with the treated side up. Then, 1 ml of 0.9% NaCl was added onto the tissue material. The pH was then measured directly on the tissue surface with a flat pH electrode. The pH value was measured at three different points and later reported as an average of the three points. Results are shown in Table 1.

TABLE 1

Surface pH measurements for different concentrations of lactic acid added to the tissue

| Sample | pH value |
| --- | --- |
| Ref. | 6.6 |
| 0.5 g/m$^2$ lactic acid buffer | 3.5 |
| 1.5 g/m$^2$ lactic acid buffer | 3.5 |
| 2.5 g/m$^2$ lactic acid buffer | 2.9 |

Method 2—Extracted pH ISO 6588-1 (without KCl) 2 g material was submersed in 100 ml distilled water and left to soak for 1 h. Shaking was performed after 30 minutes. The material was removed and the pH was measured in the remaining liquid. The result is shown in Table 2 below.

TABLE 2

Extracted pH measurements for different concentrations
of lactic acid added to the tissue.

| Sample | pH value |
|---|---|
| Ref. | 7.4 |
| 0.5 g/m² lactic acid buffer | 3.8 |
| 1.5 g/m² lactic acid buffer | 3.5 |
| 2.5 g/m² lactic acid buffer | 3.3 |

Example 5: Water Activity of Tissue Paper Product

Water activity was measured using 4 sheets of the different samples. The samples were cut to completely cover the bottom of the measuring chamber. The device used was Aqua Lab Dew Point Water Activity meter 4 TE. The tissue samples were pre-conditioned at a climate of 23° C. and 35% RH.

Tissue paper was produced according to Example 3.

TABLE 3

Water activity of tissue paper untreated or treated
with lactic acid in different amounts.

| Samples | Measured water activity |
|---|---|
| Reference | 0.324 |
| 0.5 g/m² | 0.346 |
| 1.5 g/m² | 0.349 |
| 2.5 g/m² | 0.344 |

Water activity was well within limits for acceptance and very small differences were found when comparing lactic acid treated and untreated samples.

Example 6: Softness Measurements with TSA

Figure 1:
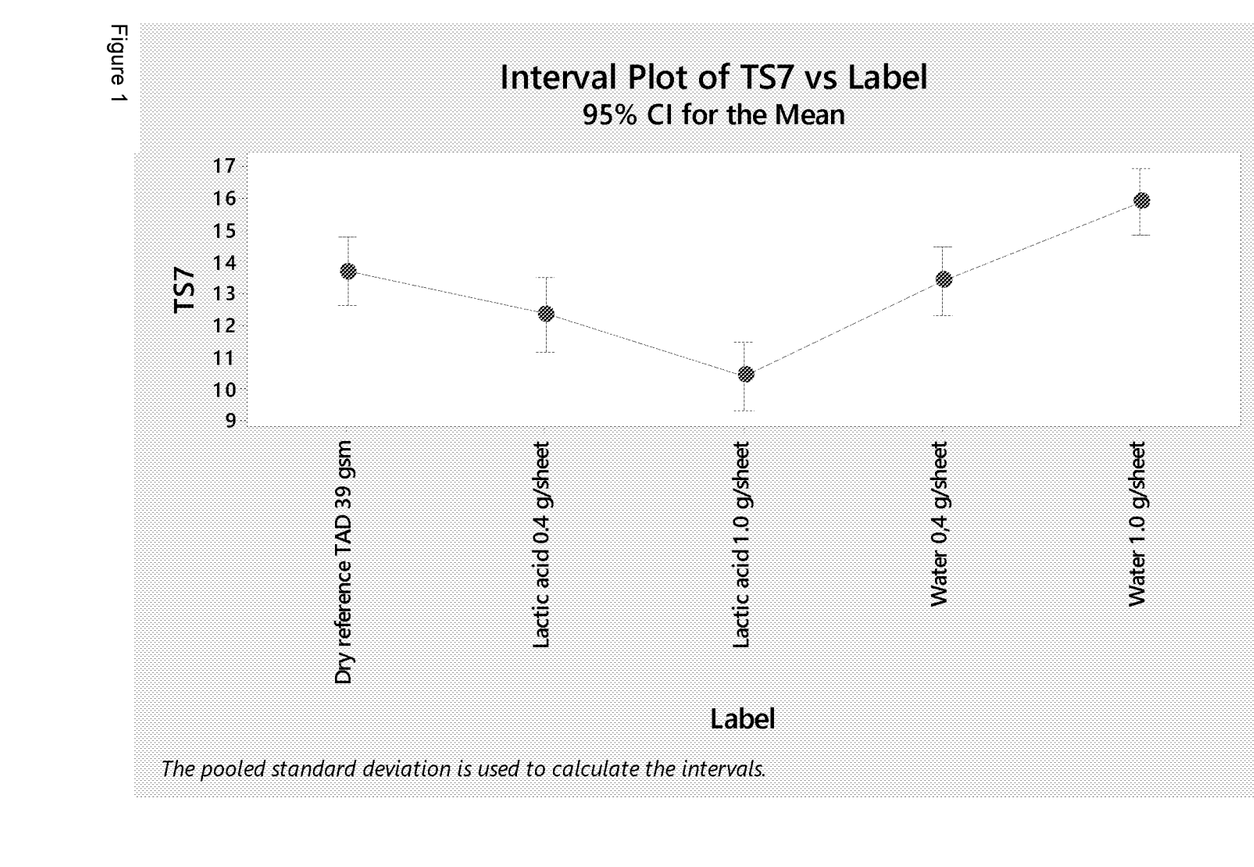
FIG. 1 is a graph showing relative TS7 Fiber Softness values, analyzed with Tissue Softness Analyzer (TSA). Lower TS7 value means softer material.
Figure 2:
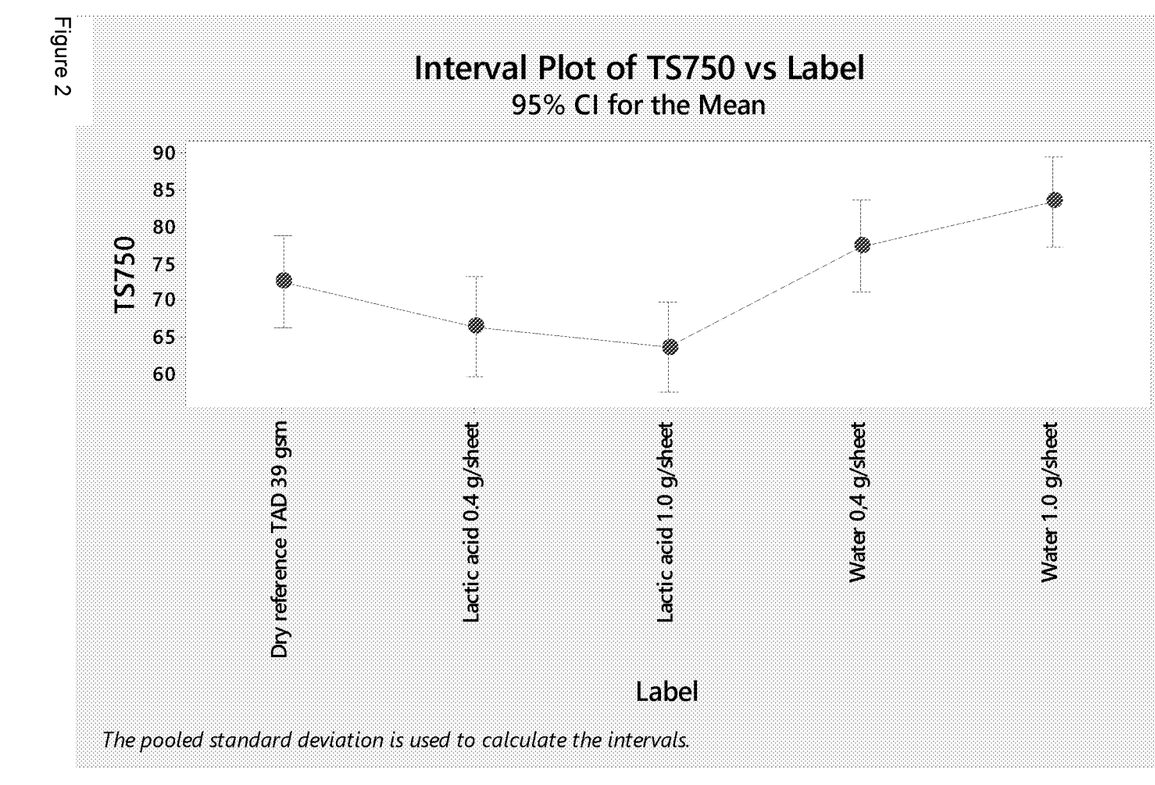
FIG. 2 is a graph showing relative TS750 Roughness values, analyzed with Tissue Softness Analyzer (TSA). Higher TS750 values correspond to higher roughness and lower values consequently means softer material.
Figure 3:
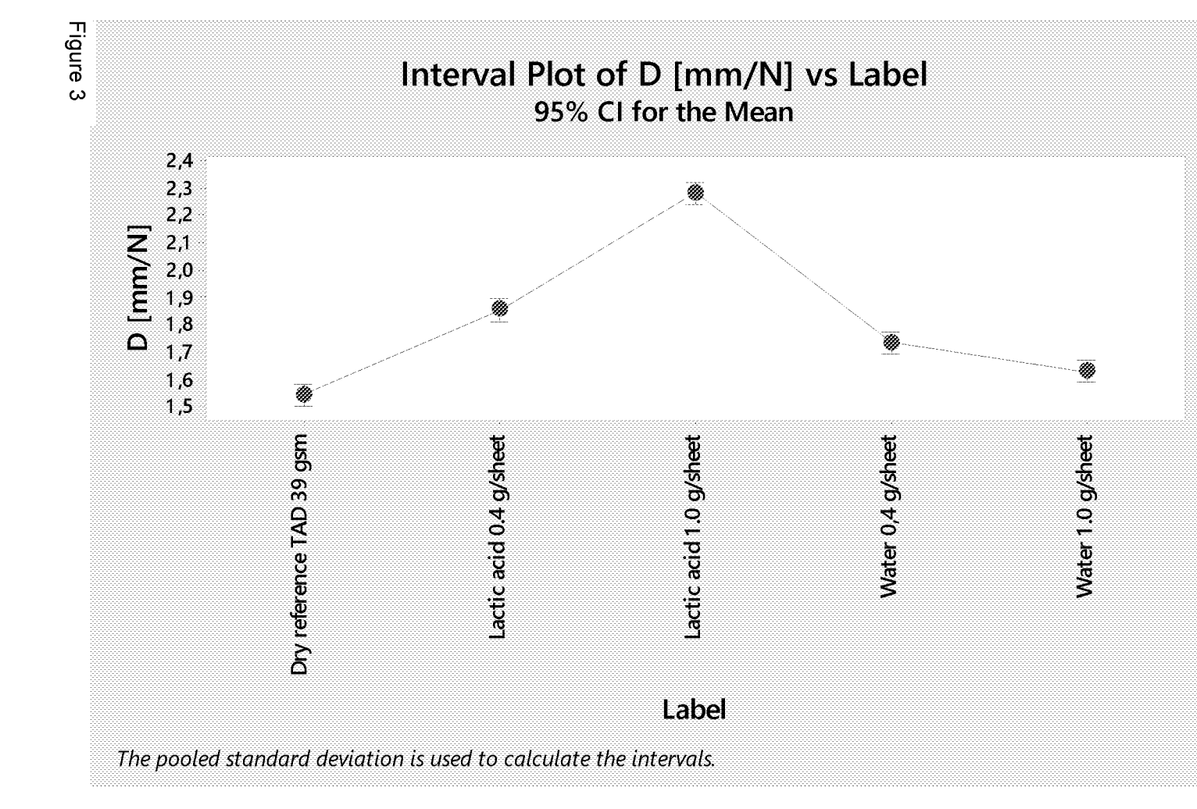
FIG. 3 is a graph showing relative D values, analyzed with the Tissue Softness Analyzer (TSA). Higher values correspond to a more flexible and textile like material.
Figure 4:
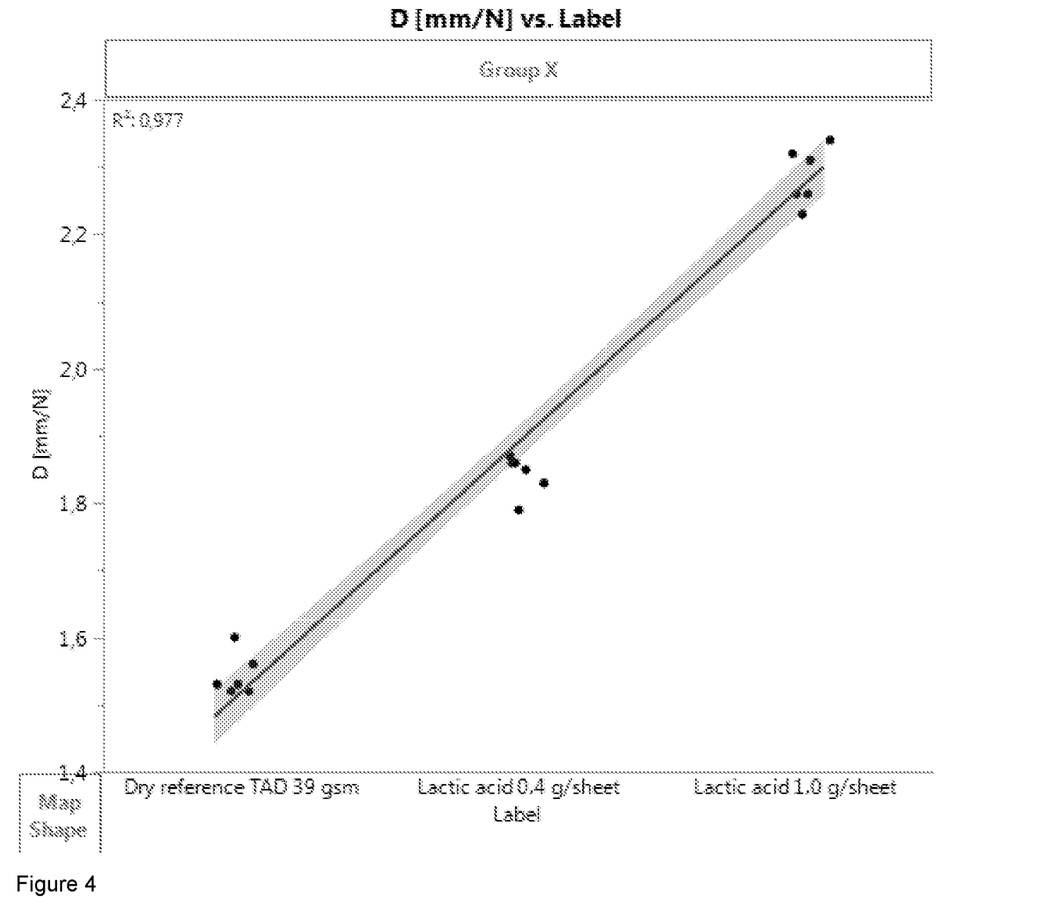
FIG. 4 is a graph showing direct correlation between D-values measured for various samples, analyzed with Tissue Softness Analyzer (TSA), and lactic acid treated samples.

Sprayed tissue samples (TAD base sheet 39 gsm, ATMOS 2-ply 41 g/m²) were measured with Tissue Softness Analysis. Samples were cut in round pieces with a diameter of 112.8 mm. The measuring area, with a diameter of 70 mm, did not contain any folding or printing. The samples were fixed on the drumhead and the measurements were performed according to the method. Every sample was measured 6 times and finally the average of these six measurements was reported for the parameters TS7, TS750 and the D-value, see Table 4 and FIGS. 1-4.

Results TSA Method
Material 1: TAD 1-ply 39 g/m²

TABLE 4

Softness values for tissue paper treated with lactic acid.

| Sample, TAD 39 g/m² | TS7 | TS750 | D [mm/N] |
|---|---|---|---|
| Untreated ref | 13.7 | 72.6 | 1.54 |
| Water 0.4 g/m² | 13.4 | 77.5 | 1.74 |
| Water 1.0 g/m² | 15.9 | 83.5 | 1.63 |
| Lactic acid buffer 0.4 g/m² | 12.3 | 70.0 | 1.84 |
| Lactic acid buffer 1.0 g/m² | 10.4 | 63.6 | 2.23 |

Conclusions

The increase in D-value for the lactic acid treated samples corresponds to a less stiff and more flexible material. In this specific case, the D-values increased 45% for the TAD 1-ply 39 g/m² with 1 g/m² lactic acid buffer and 19% for the 0.4 g/m² lactic acid buffer. The term flexible refers here to a material which is more drapable and textile like. Thus, the D-values correlates well with the outcome of the panel, see Example 7.

Parameter TS7 in Table 4 above indicates a higher softness on fiber level for lactic acid treated samples compared to the references, which also correlates with panel evaluation surface softness, see Example 7.

The results of the parameter TS750 indicates a higher smoothness for both of the lactic acid treated materials compared with the references.

The mentioned parameters above are all of relevance for evaluating the experienced softness and flexibility when touching, holding, bending and folding the tissue material.

Example 7: Softness Evaluation by Panel

Softness measurements were conducted with an experienced panel consisting of 6 persons. These persons are all, trained for judging of the softness and flexibility/drapability of different tissue products. The samples were coded and randomized. The evaluation was done individually and the samples were ranked according to softness and flexibility. The panelists were given two sets of samples. The first set contained three samples, a lactic acid treated material at low level, a water treated material at a low level as well as an untreated reference. The panelists were asked to evaluate softness and flexibility by ranking the samples. Thereafter, a corresponding set of samples was provided to the panelist with higher amounts of lactic acid and water, including a untreated reference sample. Ranking was performed in the same way as with the first set.

Tissue Sample Preparation

Hand towels 2-ply ATMOS 40 gsm (21×33 cm) were manually sprayed with lactic acid buffer or pure water according to Table 5. The buffer was prepared according to Example 1. The towels were dried in room temperature for at least 24 hours.

TABLE 5

Sample preparation.

| Sample | Lactic acid buffer 9M (g/towel) | Water (g/towel) |
|---|---|---|
| Lactic acid low level | 0.4 | — |
| Lactic acid high level | 1.0 | — |
| Water low level | — | 0.4 |
| Water high level | — | 1.0 |
| Untreated reference | — | — |

Instruction for Judging Softness

"Put the samples on the table in front of you. Use your right hand if you are right handed and your left hand if you are left handed. Open your hand and put it on one of the lower corner on the material, without pressing. Move slowly your hand up to the opposite corner. Use both your palm and finger tops when evaluating the softness. Repeat the procedure for the second sample and judge the Softness. If impossible to distinguish the samples from each other, put them on the same position."

Instruction for Judging Flexibility/Drapability

"Put the samples on the table in front of you. Then, lift one paper, hold it between your hands and try to squeeze it between your fingers. Evaluate the flexibility/drapability i.e. how easy the material can be formed. Repeat the procedure for the second and the third sample and rank the samples from least flexible to most flexible. Use the scale below. If impossible to distinguish the samples from each other, put them on the same position."

TABLE 6

Softness evaluation

| Experienced Softness | No of persons (tot 6) |
|---|---|
| Lactic acid treated low level ranked as softer than water treated reference and dry reference | 6 |
| Lactic acid treated high level ranked as softer than water treated reference and dry reference | 6 |

TABLE 7

Flexibility evaluation results

| Experienced Flexibility | No of persons (tot 6) |
|---|---|
| Lactic acid treated low level ranked as more flexible than water treated reference and dry reference | 6 |
| Lactic acid treated high level ranked as more flexible than water treated reference and dry reference | 6 |

Conclusions

Softness: All the panelists ranked the lactic acid treated material as softer than both the water treated material and the dry reference at both high and low level.

Flexibility: All the panelists experienced better flexibility/drapability with the lactic acid treated material compared with water treated reference and dry reference at both high and low level.

Example 8: Impact of Lactic Acid on Skin pH

Skin Study 1

Skin pH on the forearm was measured before and after wiping with the tissue treated with lactic acid. The pH meter used was pH 1000 L with flat probe Hamilton flattrode. The pH meter rod was rinsed with saline solution (0.9% NaCl) before each new measurement. The rinsing of the pH electrode left a small droplet of saline hanging from the electrode, which was used to wet the skin on the volar forearm at the point of measurement. All the pH measurements were performed in a climatized room, at 23° C. and 50% RH.

The pH was measured on the forearm of two volunteers (before value). The measured spot on the arm, was wiped gently (3 swipes) with a small piece of test tissue with the addition of 5 droplets of saline. pH was measured again on the same spot of the arm. For each new tissue tested a new spot on the arm was selected and pH measured again before and after wiping. The results can be seen in Table 8. The conclusion is that pH is decreased after wiping with tissue containing lactic acid.

TABLE 8 pH of skin before and after wiping with tissue paper products with different amounts of lactic acid.

| Tissue | Person 1 before wiping | Person 1 after wiping | Person 2 before wiping | Person 2 after wiping |
|---|---|---|---|---|
| Reference - no addition of lactic acid | 5.5 | 5.5 | 5.6 | 5.7 |
| Tissue with 0.5 g/m² buffered lactic acid | 5.6 | 4.7 | 5.5 | 4.8 |
| Tissue with 1.5 g/m² buffered lactic acid | 5.4 | 3.7 | 5.4 | 3.9 |
| Tissue with 2.5 g/m² buffered lactic acid | 5.5 | 3.9 | 5.6 | 3.6 |

Skin Study 2

A skin study was performed to evaluate if use of a lactic acid-treated paper towel will result in a decreased skin pH. The test was performed on 21 test persons. None of the test persons had applied hand cream or hand lotion on the hands from the evening before.

Test Procedure

The test persons were asked to wash their hands with soap and rinse carefully with water. They were advised to shake away water droplets and then dry their hands with a tissue paper hand towel. The average time for toweling was 10 seconds. In the first session, a reference towel without lactic acid was used for toweling and in the following session a lactic acid treated towel was used, see Table 9. The test persons were asked to wait 4 hours between the two testing sessions. The pH was measured at three places of the hands, finger tips, palm and the back of the hands before and after wiping with the towels. A delta pH value of before and after wiping was reported for every test person. After wiping with the lactic acid treated hand towel the pH measurements were repeated after 15 min to define if the eventually pH decrease remains over time.

Samples 1. Dry reference paper hand towel 2. Lactic acid treated paper hand towel, produced according to Example 3.

TABLE 9

Average value of delta pH before and after wiping with Sample 1 and 2. Delta pH values before and after 15 min are also presented for sample 2.

| Spot | Difference: Before – After | Standard deviation | Difference: Before – After 15 min | Standard deviation |
|---|---|---|---|---|
| Index finger, Sample 2 | 1.1 | 0.3 | 0.6 | 0.3 |
| Palm, Sample 2 | 0.3 | 0.2 | 0.2 | 0.2 |
| Back of the hand, Sample 2 | 0.9 | 0.4 | 0.8 | 0.4 |
| Index finger, Sample 1 | 0.0 | 0.2 | — | — |
| Palm, Sample 1 | −0.3 | 0.2 | — | — |
| Back of the hand, Sample 1 | −0.1 | 0.2 | — | — |

Conclusions

A pH decrease of approximately one pH unit was obtained on the index finger and on the back of the hand, after wiping with the lactic acid treated towel for about 10 seconds. The skin pH values decreased generally from 5 to 4 for the lactic acid treated material. No significant difference in skin pH was obtained for the reference sample. The delta pH values after waiting time indicated that this effect is partly kept after 15 minutes. The pH difference was less in the palm than on the fingertip and on the back of the hand. The pH decrease confirms that we have a transfer of lactic acid from the material onto the skin. As this pH decreased and controlled skin pH is associated with better skin health, the result indicates that a lactic acid treated towel is more beneficial to the skin than an untreated towel.

The embodiments described above are only descriptions of preferred embodiments of the present invention, and are not intended to limit the scope of the invention. Various variations and modifications can be made to the technical solution of the present invention by those of ordinary skill in the art, without departing from the design of the present invention. The variations and modifications should all fall within the claimed scope defined by the claims of the invention.

What is claimed is:

1. A fibrous product comprising:
a fibrous material that is at least one of a tissue paper material, a nonwoven material, and a mixed tissue paper and nonwoven material, and
a dry coating applied to the fibrous material that comprises at least one of lactic acid and a salt thereof in an amount of from about 0.1 to about 15 $g/m^2$;
wherein the fibrous product is at least one of a hand towel, handkerchief, facial, dry wipe, napkin, washcloth, cleaning cloth, household towel, wiping tissue and toilet paper;
wherein the fibrous product has a pH of 3.0 to 3.5; and
wherein the fibrous product has a flexibility increase of at least about 10% measured as a D-value, compared to an identical fibrous material without the dry coating, and the fibrous product has a softness increase defined by at least about 15% lower TS7-value, compared to the identical fibrous material without the dry coating.

2. The fibrous product according to claim 1, wherein a water activity of said fibrous product is from about 0.03 to about 0.85.

3. The fibrous product according to claim 2, wherein the water activity of said fibrous product is from about 0.1 to about 0.65.

4. The fibrous product according to claim 2,
wherein said salt of lactic acid is at least one of sodium lactate, potassium lactate and calcium lactate,
wherein said fibrous material further comprises one or more pH regulating substances,
wherein said at least one of the lactic acid and the salt thereof is provided to at least one of outer surfaces of the fibrous product, and
wherein said fibrous product is either a multi-ply product or a one-ply product.

5. The fibrous product according to claim 1, wherein said salt of lactic acid is at least one of sodium lactate, potassium lactate and calcium lactate.

6. The fibrous product according to claim 1, wherein said fibrous material further comprises one or more pH regulating substances.

7. The fibrous product according to claim 1, wherein said at least one of the lactic acid and the salt thereof is provided to at least one of outer surfaces of the fibrous product.

8. The fibrous product according to claim 1, wherein said fibrous product is a multi-ply product.

9. The fibrous product according to claim 1, wherein said fibrous product is a one-ply product.

10. The fibrous product according to claim 1, wherein said fibrous material comprises at least one of lactic acid and a salt thereof in an amount of from about 1.0 to about 1.5 $g/m^2$.

11. The fibrous product according to claim 1, wherein the dry coating applied to the fibrous material results in the at least one of lactic acid and a salt thereof to be applied in an amount of at least 0.1 $g/m^2$ and less than 1.0 $g/m^2$.

12. A method for improving a softness of a fibrous material comprised in a fibrous product as defined in claim 1, the method comprising:
(a) providing a fibrous material;
(b) providing a composition comprising at least one of lactic acid and a salt thereof to the fibrous material; and
(c) drying the fibrous material to a water activity of about 0.85 or less to provide a fibrous product having an improved softness.

13. A method for producing a fibrous product comprising a fibrous material wherein the fibrous material comprises at least one of lactic acid and a salt thereof in an amount of from about 0.1 to about 15 $g/m^2$, wherein the fibrous product has a water activity of about 0.85 or less, and the method comprises:
(a) providing the fibrous material;
(b) providing a composition comprising at least one of lactic acid and a salt thereof to the fibrous material; and
(c) drying the fibrous material provided with the composition comprising at least one of the lactic acid and the salt thereof to provide a fibrous product;
wherein the fibrous product is as defined in claim 1.

14. The method according to claim 13, wherein the composition comprising at least one of the lactic acid and the salt thereof is provided to the fibrous material by coating.

15. The method according to claim 13, wherein the drying of the fibrous material is performed by air drying or IR drying.

16. The method according to claim 13, wherein in step (b) the composition comprising at least one of the lactic acid and the salt thereof is provided to at least one of outer surfaces of the fibrous product.

17. The method according to claim 13, wherein the fibrous material comprises at least one of lactic acid and a salt thereof in an amount of from about 1.0 to about 1.5 $g/m^2$.

18. The method according to claim 13, wherein the dry coating applied to the fibrous material in step (b) results in the at least one of lactic acid and a salt thereof to be applied in an amount of at least 0.1 $g/m^2$ and less than 1.0 $g/m^2$.

* * * * *